(12) United States Patent
Yasuda et al.

(10) Patent No.: US 9,696,206 B2
(45) Date of Patent: Jul. 4, 2017

(54) TERAHERTZ-WAVE SPECTROMETER

(75) Inventors: Takashi Yasuda, Hamamatsu (JP);
Kouichiro Akiyama, Hamamatsu (JP);
Yoichi Kawada, Hamamatsu (JP);
Atsushi Nakanishi, Hamamatsu (JP);
Hironori Takahashi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/005,841

(22) PCT Filed: Feb. 21, 2012

(86) PCT No.: PCT/JP2012/054159
§ 371 (c)(1),
(2), (4) Date: Sep. 18, 2013

(87) PCT Pub. No.: WO2012/132647
PCT Pub. Date: Oct. 4, 2012

(65) Prior Publication Data
US 2014/0014840 A1 Jan. 16, 2014

(30) Foreign Application Priority Data

Mar. 29, 2011 (JP) ................................. 2011-072408

(51) Int. Cl.
*G01N 5/02* (2006.01)
*G01J 3/42* (2006.01)
*G01N 21/3581* (2014.01)

(52) U.S. Cl.
CPC ............ *G01J 3/42* (2013.01); *G01N 21/3581* (2013.01)

(58) Field of Classification Search
CPC ....... G01J 3/42; G01N 21/3581; G01N 21/27; G01N 35/10; G01N 21/358
(Continued)

(56) References Cited

U.S. PATENT DOCUMENTS 4,602,869 A 7/1986 Harrick
6,958,853 B1 10/2005 Arnone et al.
(Continued)

FOREIGN PATENT DOCUMENTS

DE 37 15 481 11/1988
DE 383002 A1 * 1/1990
(Continued)

OTHER PUBLICATIONS

Translation of JP 2007-271361A.*
(Continued)

*Primary Examiner* — David Porta
*Assistant Examiner* — Mamadou Faye
(74) *Attorney, Agent, or Firm* — Drinker Biddle & Reath LLP

(57) ABSTRACT

In a terahertz-wave spectrometer, a spectroscopic prism is provided with a prism part slidable with respect to a main part thereof. Along the sliding direction, an arrangement surface in an upper face of the prism part is provided with a plurality of arrangement regions K to be arranged with objects to be measured. Therefore, after completing the measurement of optical constants for one object, the prism part is slid, so as to shift the next object onto an optical path of a terahertz wave T, whereby a plurality of objects can be measured smoothly without cleaning the arrangement surface.

4 Claims, 10 Drawing Sheets

(58) Field of Classification Search
USPC .................................................. 250/339.07
See application file for complete search history.

(56) References Cited

U.S. PATENT DOCUMENTS

| | | | |
|---|---|---|---|
| 2002/0067480 A1* | 6/2002 | Takahashi .................... | 356/317 |
| 2003/0227668 A1 | 12/2003 | Imai et al. | |
| 2004/0114148 A1 | 6/2004 | Agladze et al. | |
| 2005/0112784 A1* | 5/2005 | Yguerabide ......... | C12Q 1/6816 |
| | | | 436/518 |
| 2006/0066942 A1* | 3/2006 | Kouno et al. ................. | 359/368 |
| 2006/0231762 A1 | 10/2006 | Ohtake et al. | |
| 2007/0229094 A1 | 10/2007 | Kasai et al. | |
| 2008/0014580 A1 | 1/2008 | Alfano et al. | |
| 2008/0239317 A1 | 10/2008 | Schulkin et al. | |
| 2008/0259428 A1* | 10/2008 | Zimdars et al. ............. | 359/211 |
| 2008/0265165 A1 | 10/2008 | Yeh et al. | |
| 2009/0225312 A1 | 9/2009 | Formanek et al. | |
| 2009/0283680 A1 | 11/2009 | Logan, Jr. et al. | |
| 2010/0091266 A1* | 4/2010 | Yasuda ................ | G01N 21/552 |
| | | | 356/51 |
| 2011/0006226 A1 | 1/2011 | Schulkin et al. | |
| 2011/0057109 A1 | 3/2011 | Guo et al. | |
| 2012/0113417 A1 | 5/2012 | Linfield et al. | |
| 2014/0008540 A1* | 1/2014 | Yasuda et al. ........... | 250/339.07 |
| 2014/0008541 A1* | 1/2014 | Akiyama et al. ......... | 250/339.11 |

FOREIGN PATENT DOCUMENTS

| | | | | |
|---|---|---|---|---|
| DE | 3830002 A1 | * | 3/1990 | ......... G01N 21/0303 |
| EP | 1 630 542 A1 | | 3/2006 | |
| EP | 1 998 163 | | 12/2008 | |
| EP | 2273254 A1 | | 1/2011 | |
| JP | 61-232412 | | 10/1986 | |
| JP | H11-037922 | | 2/1999 | |
| JP | 2000-065729 | | 3/2000 | |
| JP | 2000-121551 | * | 4/2000 | |
| JP | 2000-121551 A | | 4/2000 | |
| JP | 2004-093495 A | | 3/2004 | |
| JP | 2006-200931 A | | 8/2006 | |
| JP | 2007-024540 A | | 2/2007 | |
| JP | 2007-271361 A | * | 10/2007 | |
| JP | 2007-271361 A | | 10/2007 | |
| JP | 2007-279025 A | | 10/2007 | |
| JP | 2008-224449 A | | 9/2008 | |
| JP | 2008-224451 A | | 9/2008 | |
| JP | 2008-224452 A | | 9/2008 | |
| JP | 2008-224449 | * | 11/2008 | |
| JP | 2010-014642 | | 1/2010 | |
| WO | WO 02/18919 | | 3/2002 | |
| WO | WO 2006/051778 | | 5/2006 | |

OTHER PUBLICATIONS

Translation of DE 3830002A1.*
Translation of DE 3830002-A1.*
U.S. Office Action dated Oct. 21, 2014 that issued in U.S. Appl. No. 14/005,849 including Double Patenting Rejections on pp. 2-5.
International Search Report dated Oct. 10, 2013 issued in International Application No. PCT/JP2012/054157.
Supplementary European Search Report dated Aug. 12, 2014 issued in European Application No. 12763373.3-1554/2693199 PCT/JP2012054157.

* cited by examiner

TERAHERTZ-WAVE SPECTROMETER

TECHNICAL FIELD

The present invention relates to a terahertz-wave spectrometer which uses a terahertz wave.

BACKGROUND ART

Conventionally known as an example of techniques relating to a spectrometer using a terahertz wave is a total reflection terahertz-wave spectrometer described in Patent Literature 1. In this total reflection terahertz-wave spectrometer, an entrance surface of an internal total reflection prism is integrally provided with a terahertz-wave generator, while an exit surface of the internal total reflection prism is integrally provided with a terahertz-wave detector. Using such an integral prism integrating the internal total reflection prism, terahertz-wave generator, and terahertz-wave detector together is advantageous in that it can detect the generation of terahertz waves at high efficiency while reducing the size of the total reflection spectrometer.

CITATION LIST

Patent Literature

Patent Literature 1: Japanese Patent Application Laid-Open No. 2008-224449

SUMMARY OF INVENTION

Technical Problem

In the above-mentioned conventional spectrometer, an object to be measured is arranged in the upper face of the integral prism, and a correlation between a terahertz wave reflected by the upper face and probe light is detected by the terahertz-wave detector, so as to measure optical constants of the object. In the measurement using such an integral prism, however, the upper face of the integral prism must be cleaned upon each measurement operation, thus requiring further contrivances for measuring a plurality of objects smoothly.

For overcoming the problem mentioned above, it is an object of the present invention to provide a terahertz-wave spectrometer which can smoothly measure a plurality of objects.

Solution to Problem

For achieving the above-mentioned object, the terahertz-wave spectrometer in accordance with the present invention comprises a light source for emitting laser light; a branching unit for splitting the laser light emitted from the light source into pump light and probe light; a terahertz-wave generator for generating a terahertz wave in response to the pump light incident thereon after branching off at the branching unit; a spectroscopic prism, having entrance and exit surfaces for the terahertz wave and an arrangement surface for an object to be measured, for propagating therewithin the terahertz wave incident on the entrance surface, causing the arrangement surface to reflect or transmit therethrough the terahertz wave, and then emitting the terahertz wave from the exit surface; and a terahertz-wave detector for receiving the terahertz wave emitted from the exit surface of the spectroscopic prism and the probe light branching off at the branching unit and detecting a correlation between the terahertz wave and the probe light; wherein, in the spectroscopic prism, a prism part including the arrangement surface is slidable with respect to a main part, while a plurality of arrangement regions to be arranged with the object are provided in the arrangement surface in the prism part along a sliding direction.

In this terahertz-wave spectrometer, a prism part slidable with respect to a main part is provided in a spectroscopic prism. Along a sliding direction, an arrangement surface in the prism part is provided with a plurality of arrangement regions to be arranged with objects to be measured. Therefore, after measuring optical constants concerning one object, the prism part may be slid so as to move the next object onto an optical path of the terahertz wave, whereby a plurality of objects can be measured smoothly.

Preferably, the arrangement surface in the prism part is further provided with a reference region to be arranged with no object. This makes it possible to continuously perform the measurement from the reference to the objects.

Preferably, the prism part is provided with a lug. This makes it easy to slide the prism part with respect to the main part and remove the prism part from the main part.

Preferably, a space exists in a part between the prism part and the main part. This makes it easy to slide the prism part with respect to the main part and remove the prism part from the main part.

Advantageous Effects of Invention

The present invention can smoothly measure a plurality of objects.

DESCRIPTION OF EMBODIMENTS

In the following, preferred embodiments of the terahertz-wave spectrometer in accordance with the present invention will be explained in detail with reference to the drawings.

Figure 1:
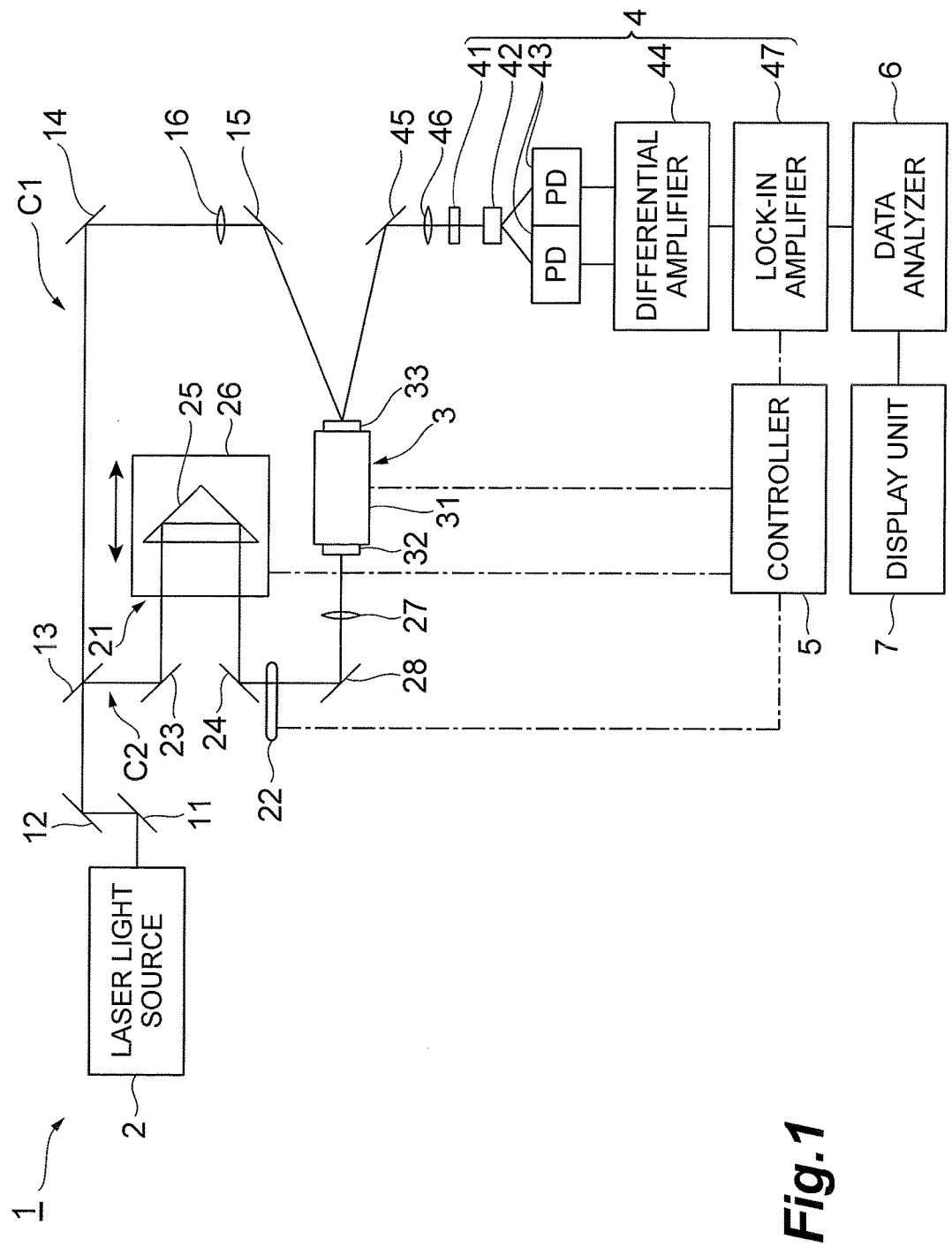
FIG. 1 is a diagram illustrating an embodiment of the terahertz-wave spectrometer in accordance with the present invention.

FIG. 1 is a diagram illustrating an embodiment of the terahertz-wave spectrometer in accordance with the present invention. As illustrated in the drawing, this terahertz-wave spectrometer 1 comprises a laser light source 2 for emitting laser light, an integral prism 3 in which a terahertz-wave generator 32, a spectroscopic prism 31, and a terahertz-wave detector 33 are integrated together, and a detection unit 4 for detecting a terahertz wave. The terahertz-wave spectrometer 1 also comprises a controller 5 for controlling operations of the constituents mentioned above, a data analyzer 6 for analyzing data according to an output from the detection unit 4, and a display unit 7 for displaying results of processing in the data analyzer 6.

The laser light source 2 is a light source for generating a femtosecond pulsed laser. The laser light source 2 issues a femtosecond pulsed laser having an average power of 120 mW and a repetition rate of 77 MHz, for example. The femtosecond pulsed laser emitted from the laser light source 2 impinges on mirrors 11, 12 in sequence and then is split into two, i.e., pump light 48 and probe light 49, by a beam splitter 13. A probe light optical path C1 through which the probe light 49 propagates is provided with mirrors 14, 15 and a lens 16, so that the probe light 49 is converged by the lens 16, so as to be made incident on a terahertz-wave detector 33 which will be explained later.

On the other hand, a pump light optical path C2 through which the pump light 48 propagates is provided with a delay unit 21 and a modulator 22. The delay unit 21, which is constructed by a pair of mirrors 23, 24 and a reflection prism 25 disposed on a movable stage 26, can adjust a delay in the pump light 48 by moving the position of the reflection prism 25 back and forth with respect to the pair of mirrors 23, 24. The modulator 22 is a part which switches between transmitting and blocking the pump light 48 by an optical chopper, for example. According to a signal from the controller 5, the modulator 22 modulates the switching between transmitting and blocking the pump light 48 at 1 kHz, for example.

Figure 2:
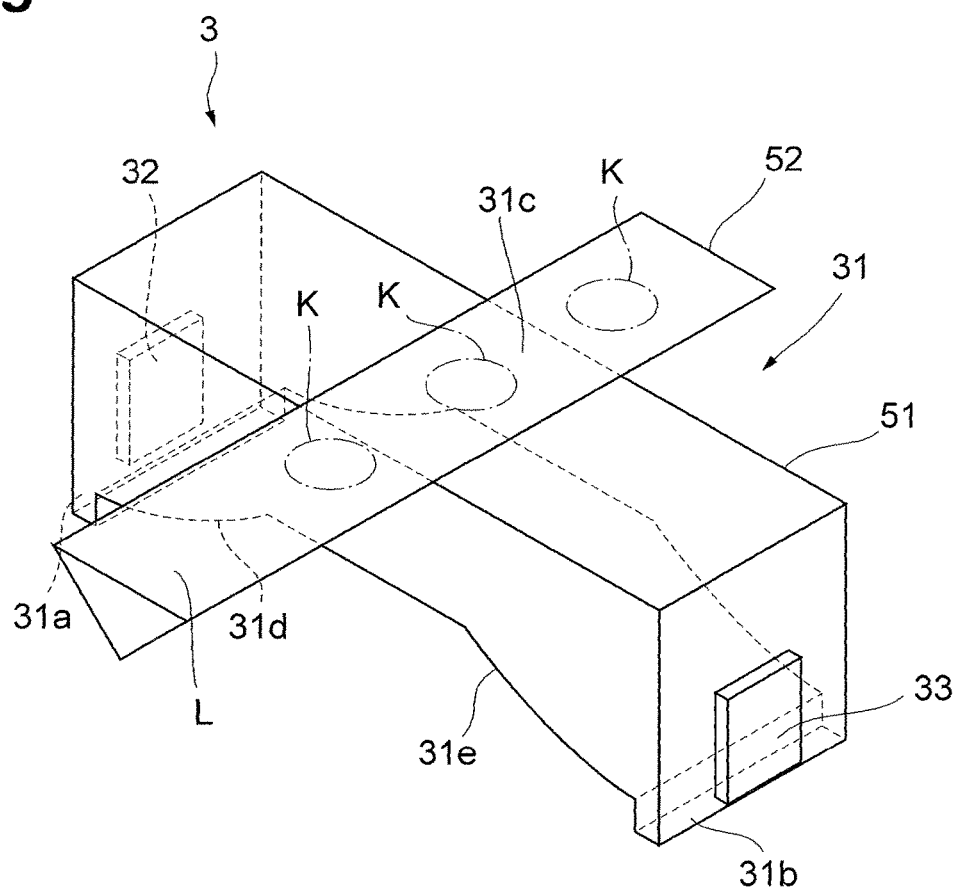
FIG. 2 is a perspective view of an integral prism used in the terahertz-wave spectrometer illustrated in FIG. 1.
Figure 3:
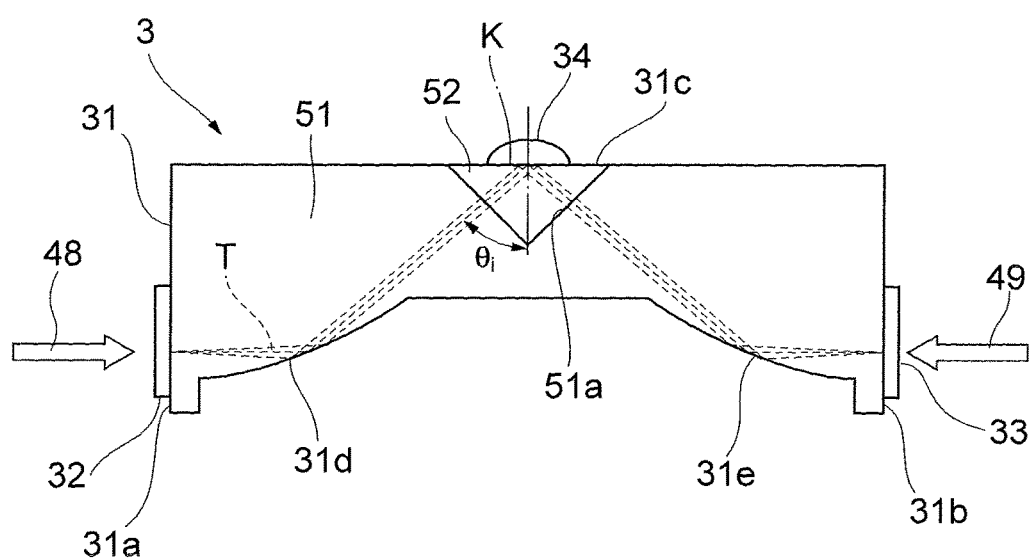
FIG. 3 is a side view of FIG. 2.

The pump light 48 propagated through the pump light optical path C2 impinges on a mirror 28 and then is converged by a lens 27, so as to be made incident on the integral prism 3. As illustrated in FIGS. 2 and 3, the spectroscopic prism 31 constituting the integral prism 3, which is formed by Si, for example, has an entrance surface 31a to which the terahertz-wave generator 32 is integrally secured and an exit surface 31b to which the terahertz-wave detector 33 is integrally secured. The upper face of the spectroscopic prism 31 forms an arrangement part 31c to be arranged with an object to be measured 34, from which various optical constants such as refractive index, dielectric constant, and absorption coefficient are measured.

In the bottom face of the spectroscopic prism 31, as illustrated in FIG. 3, a first optical surface 31d for collimating the terahertz wave T generated in the terahertz-wave generator 32 toward the arrangement part 31c is provided between the entrance surface 31a and the arrangement part 31c. A second optical surface 31e for converging the terahertz wave T from the arrangement part 31c toward the exit surface 31b is provided between the arrangement part 31c and the exit surface 31b. The first and second optical surfaces 31d, 31e are formed by curving the bottom face of the spectroscopic prism 31 into a predetermined form.

Nonlinear optical crystals of ZnTe and the like, antenna elements such as optical switches using GaAs, semiconductors such as InAs, and superconductors, for example, can be used as the terahertz-wave generator 32. The pulse of the terahertz wave T generated from these elements is in the order of several picoseconds in general. When a nonlinear optical crystal is used as the terahertz-wave generator 32, the pump light 48 incident on the terahertz-wave generator 32, if any, is converted into the terahertz wave T by a nonlinear optical effect.

Electrooptical crystals of ZnTe and the like and antenna elements such as optical switches using GaAs, for example, can be used as the terahertz-wave detector 33. When the terahertz wave T and the probe light 49 are incident on the terahertz-wave detector 33 at the same time in the case where an electrooptical crystal is used as the terahertz-wave detector 33, the probe light 49 incurs birefringence due to the Pockels effect. The amount of birefringence in the probe light 49 is in proportion to the electric field intensity of the terahertz wave T. Therefore, detecting the amount of birefringence of the probe light 49 makes it possible to sense the terahertz wave T.

For example, a thermosetting adhesive is used for securing the terahertz-wave generator 32 and the terahertz-wave detector 33. Preferably, the adhesive used here is transparent at the wavelength of the terahertz wave T and has a refractive index in the middle between or equivalent to each of the respective refractive indexes of the terahertz-wave generator 32 and terahertz-wave detector 33 and the refractive index of the spectroscopic prism 31.

A wax transparent at the wavelength of the terahertz wave T may be melted and coagulated in place of the adhesive, or marginal parts of the terahertz-wave generator 32 and terahertz-wave detector 33 may be secured with the adhesive while the terahertz-wave generator 32 and terahertz-wave detector 33 are in direct contact with the entrance surface 31a and exit surface 31b, respectively.

When the terahertz-wave detector 33 is an electrooptical crystal, the detection unit 4 for detecting the terahertz wave is constituted by a quarter wave plate 41, a polarizer 42, a pair of photodiodes 43, 43, a differential amplifier 44, and a lock-in amplifier 47, for example, as illustrated in FIG. 1. The probe light 49 reflected by the terahertz-wave detector 33 is guided by the mirror 45 toward the detection unit 4, converged by a lens 46, so as to be transmitted through the quarter wave plate 41, and then separated by the polarizer 42, which is a Wollaston prism or the like, into vertical and horizontal linearly polarized light components. The vertical and horizontal linearly polarized light components are converted into their respective electric signals by the pair of photodiodes 43, 43, while the difference therebetween is detected by the differential amplifier 44. The output signal from the differential amplifier 44 is amplified by the lock-in amplifier 47 and then fed to the data analyzer 6.

The differential amplifier 44 outputs a signal having an intensity in proportion to the electric field intensity of the terahertz wave T when the terahertz wave T and the probe light 49 are incident on the terahertz-wave detector 33 at the same time, but no signal when not. An evanescent wave emitted when the terahertz wave T is reflected by the arrangement part 31c of the spectroscopic prism 31 interacts with the object 34 arranged on the arrangement part 31c of the spectroscopic prism 31, thereby changing the reflectance of the terahertz wave T from that in the case where the object 34 is not in place. Therefore, measuring the change in reflectance of the terahertz wave T can evaluate the spectroscopic characteristic of the object 34.

The data analyzer 6 is a part which performs data analysis processing of spectrometry according to an analysis program exclusively used by the terahertz-wave spectrometer 1, for example, and is physically a computer system having a CPU (central processing unit), a memory, an input device, the display unit 7, and the like. The data analyzer 6 executes data analysis processing according to a signal fed from the lock-in amplifier 47 and causes the display unit 7 to display results of analysis.

The structure of the above-mentioned integral prism 3 will now be explained in further detail.

As illustrated in FIGS. 2 and 3, the integral prism 3 has a main part 51 and a prism part 52, formed separately therefrom, having the arrangement surface 31c as the upper face. For example, the prism part 52 is formed into a triangular cross section by Si as with the main part 51 and extends longer than the width of the main part 51 in a direction intersecting the optical path of the terahertz wave T within the integral prism 3 when the main part 51 is seen from the upper face side. As the material for the prism part 52, not only Si, but MgO may also be used, for example.

On the other hand, the upper part of the main part 51 is formed with a groove 51a having a triangular cross section corresponding to the form of the prism part 52. The prism part 52 is slidable in the width direction of the main part 51 while being fitted in the groove 51a of the main part 51 without gaps.

As illustrated in FIG. 2, along the sliding direction, the upper face of the prism part 52 is provided with a plurality of (three in this embodiment) arrangement regions K to be arranged with the objects 34. An end part of the upper face of the prism part 52 is provided with a reference region L to be arranged with no object. Therefore, sliding the prism part 52 with respect to the main part 51 can continuously switch between the objects 34 located on the arrangement surface 31c reflecting the terahertz wave T and the reference.

Figure 4:
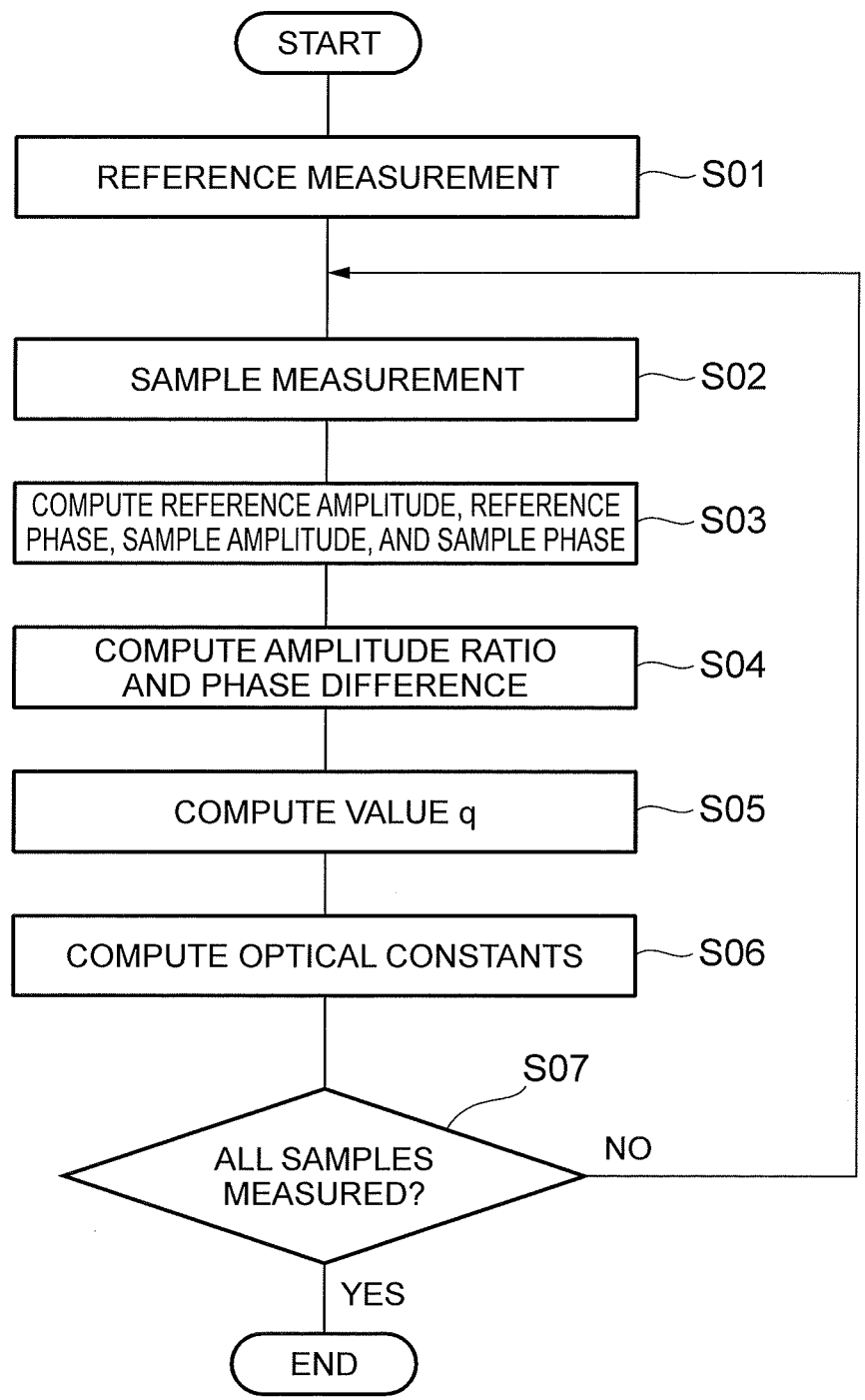
FIG. 4 is a flowchart illustrating a procedure of deriving optical constants of objects to be measured.

FIG. 4 is a flowchart illustrating a procedure of deriving optical constants of the objects 34 by using the terahertz-wave spectrometer 1. The following explanation will assume a case where the terahertz wave T is incident as p-polarized light on the arrangement surface 31c of the spectroscopic prism 31.

First, as illustrated in FIG. 4, the terahertz-wave spectrometer 1 is used for performing reference measurement and sample measurement (steps S01 and S02). In the reference measurement, while the prism part 52 is positioned with respect to the main part 51 such that the terahertz wave T propagating within the integral prism 3 is reflected by the reference region L, a material (e.g., air) having known optical constants is measured.

In the sample measurement, the prism part 52 is slid with respect to the main part 51 such that the terahertz wave T propagating within the integral prism 3 is reflected by the arrangement region K, and a material from which optical constants are to be obtained is measured. Subsequently, a reference measurement result $T_{ref}$ and a sample measurement result $T_{sig}$ are respectively Fourier-transformed, so as to determine a reference amplitude $R_{ref}$, a reference phase $\Phi_{ref}$, a sample amplitude $R_{sig}$, and a sample phase $\Phi_{sig}$ (step S03).

Next, the ratio P between the reference amplitude $R_{ref}$ and sample amplitude $R_{sig}$ is determined according to expression (1), and the phase difference $\Delta$ between the reference phase $\Phi_{ref}$ and sample phase $\Phi_{sig}$ is determined according to expression (2) (step S04).

[Math. 1]
$$P = \left| \frac{R_{sig}}{R_{ref}} \right| \tag{1}$$

[Math. 2]
$$\Delta = \Phi_{sig} - \Phi_{ref} \tag{2}$$

Further, using the above-mentioned ratio P and phase difference $\Delta$, a value q is defined as in expression (3) (step S05).

[Math. 3]
$$q = \frac{1 - Pe^{-i\Delta}}{1 + Pe^{-i\Delta}} \tag{3}$$

Here, let $\theta_i$ (see FIG. 3) be the angle at which the terahertz wave T is incident on the spectroscopic prism 31, and $\theta_{ref}$ and $\theta_{sig}$ be the respective refraction angles determined by Snell's law in the reference measurement and sample measurement. Further, using the Fresnel equations of reflection, $Pe^{-i\Delta}$ in the expression (3) can be represented by the following expression (4):

[Math. 4]
$$Pe^{-i\Delta} = \frac{\tan(\theta_i - \theta_{sig})}{\tan(\theta_i + \theta_{sig})} \cdot \frac{\tan(\theta_i + \theta_{ref})}{\tan(\theta_i - \theta_{ref})} \tag{4}$$

Substituting the above-mentioned expression (4) into the expression (3) and modifying it yields the following expression (5):

[Math. 5]
$$\sin\theta_{sig} \cdot \cos\theta_{sig} = \frac{q \cdot \sin^2\theta_i \cos^2\theta_i + \sin\theta_i \cos\theta_i \sin\theta_{ref} \cos\theta_{ref}}{\sin\theta_i \cos\theta_i + q \cdot \sin\theta_{ref} \cos\theta_{ref}} \tag{5}$$

Letting $n_{prism}$ be the complex refractive index of the material constituting the spectroscopic prism 31, and $n_{sample}$ be the complex refractive index of the object 34, the Snell's law is as in the following expression (6), while the square of the complex refractive index of the object 34 is represented by expression (7). Therefore, substituting the expression (5) into the expression (7) can determine the complex refractive index of the object 34, thereby deriving desirable optical constants of the object 34 (step S06).

[Math. 6]
$$n_{prism} \sin\theta_i = n_{sample} \sin\theta_{sig} \tag{6}$$

[Math. 7]
$$n_{sample}^2 = \frac{\sin^2\theta_i \cdot \left(1 - \sqrt{1 - 4 \cdot (\sin\theta_{sig} \cdot \cos\theta_{sig})^2}\right)}{2 \cdot (\sin\theta_{sig} \cdot \cos\theta_{sig})^2} \cdot n_{prism}^2 \tag{7}$$

After deriving the optical constants concerning one object 34 in the foregoing procedure, it is determined whether or not the measurement has been completed for all the objects 34 (step S07); when not completed, the prism part 52 is further slid, whereupon the procedure from step S02 to step S06 is repeated for the next object 34.

In the terahertz-wave spectrometer 1, as explained in the foregoing, the spectroscopic prism 31 is provided with the prism part 52 slidable with respect to the main part 51. At predetermined intervals along the sliding direction, the arrangement surface 31c of the upper face of the prism part 52 is provided with a plurality of arrangement regions K to be arranged with the objects 34. Therefore, after completing the measurement of optical constants for one object 34, the prism part 52 is slid, so as to shift the next object 34 onto the optical path of the terahertz wave T, whereby a plurality of objects 34 can be measured smoothly without cleaning the arrangement surface 31c.

In the terahertz-wave spectrometer 1, the arrangement surface 31c in the upper face of the prism part 52 is further provided with the reference region L to be arranged with no object 34. The reference region L is located at an arrangement end of the arrangement regions K, whereby the measurement can continuously be performed from the reference to the objects by sliding the prism part 52 in one direction.

The present invention is not limited to the above-mentioned embodiment.

Figure 5:
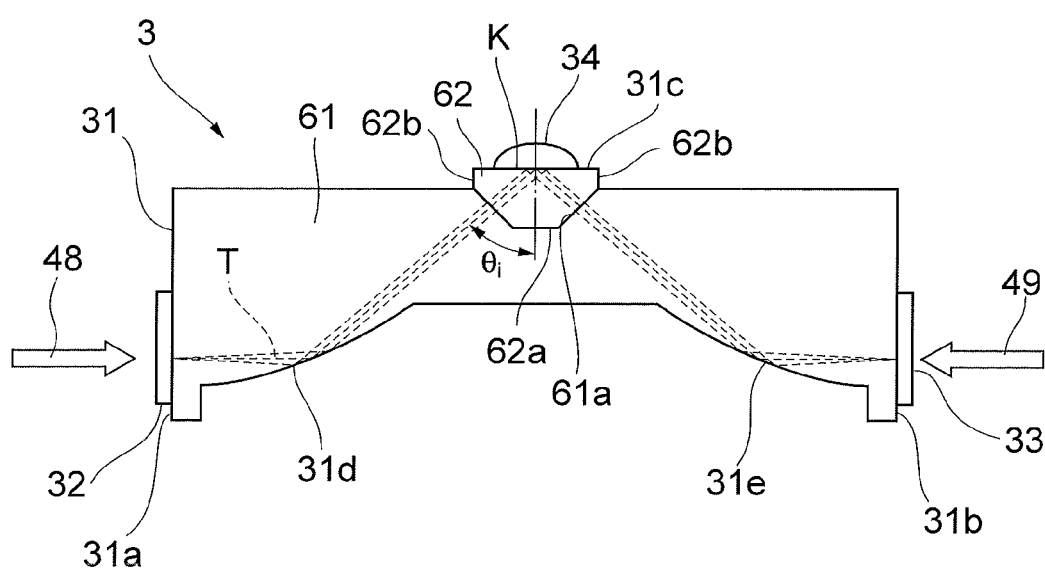
FIG. 5 is a diagram illustrating a modified example of a prism part.

For example, while the above-mentioned embodiment uses the prism part 52 having a triangular cross section, various forms can be employed for the prism part as long as they are slidable with respect to the main part while having an arrangement surface for the object and a contact surface with the main part. A modified example of the prism part may be constructed as illustrated in FIG. 5 such that the bottom face of a prism part 62 is formed with a flat surface 62a parallel to the arrangement surface 31c, while both side parts are formed with side faces 62b, 62b orthogonal to the arrangement surface 31c. The main part 61 is provided with a groove 61a corresponding to the form of the prism part 62.

Figure 6:
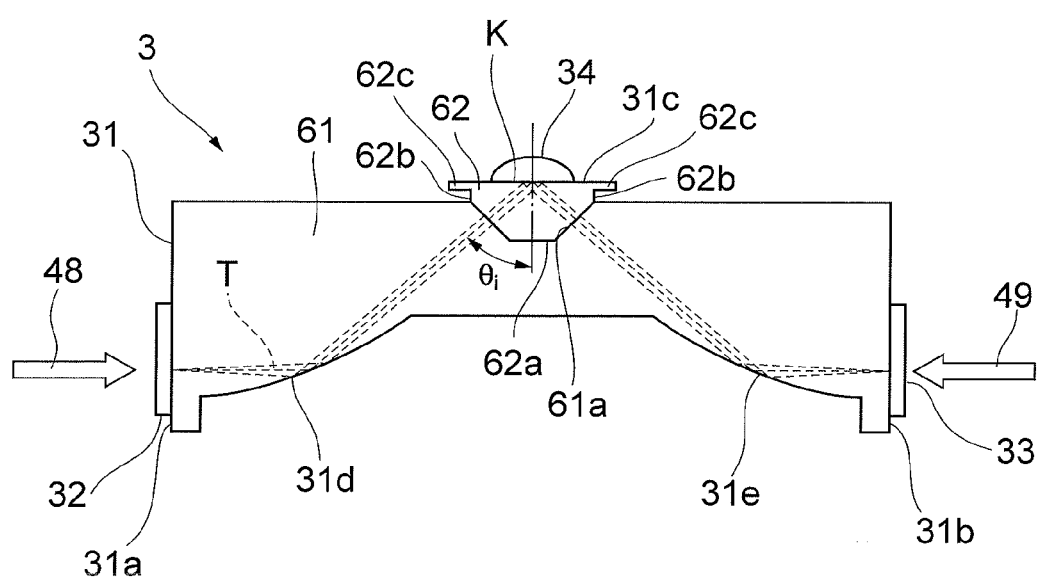
FIG. 6 is a diagram illustrating another modified example of the prism part.

Preferably, the upper face of the main part 61 is made lower than that in the case of FIG. 3 so that the side faces 62b, 62b project from the upper face of the main part 61 when the prism part 62 is fitted into the main part 61. This enables the side faces 62b, 62b to function as lugs for the prism part 62, thereby making it easy to slide, attach, and detach the prism part 62 with respect to the main part 61. For example, lugs 62c, 62c projecting like plates from the side faces 62b, 62b may further be provided as illustrated in FIG. 6. The lugs 62c, 62c make it easier to handle the prism part 62. The positions of the lugs are not restricted in particular as long as they do not inhibit the terahertz wave T from propagating and the objects 34 from being arranged.

Figure 7:
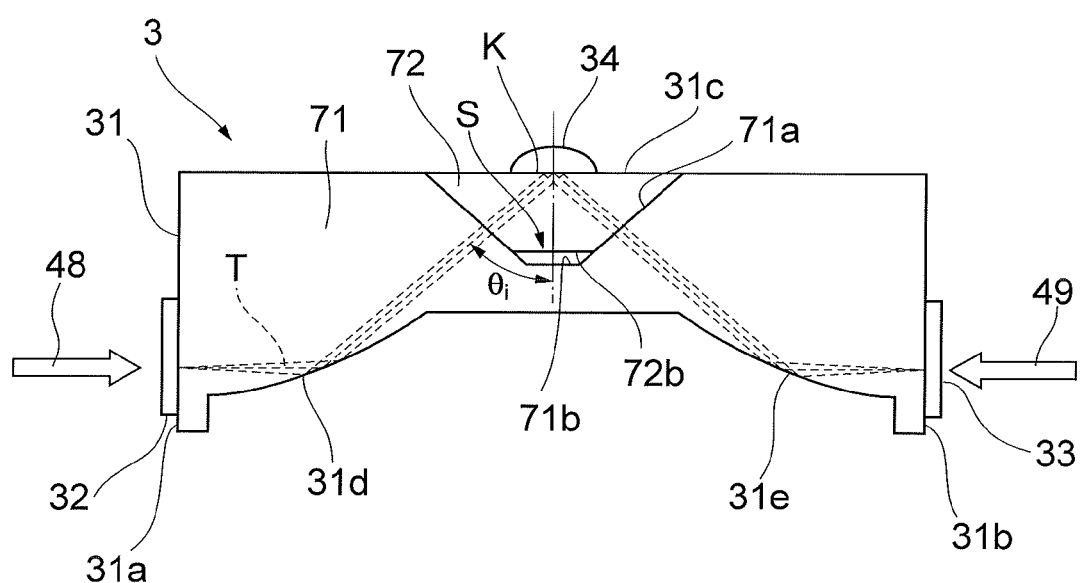
FIG. 7 is a diagram illustrating still another modified example of the prism part.

A modified example may be constructed as illustrated in FIG. 7 such that bottom parts of a groove 71a of a main part 71 and a prism part 72 are formed with respective flat surfaces 71b, 72b which are parallel to the arrangement surface 31c, while forming a space S between the flat surfaces 71b, 72b when the prism part 52 is fitted into the main part 51. This structure can also make it easy to handle the prism part 72.

Figure 8:
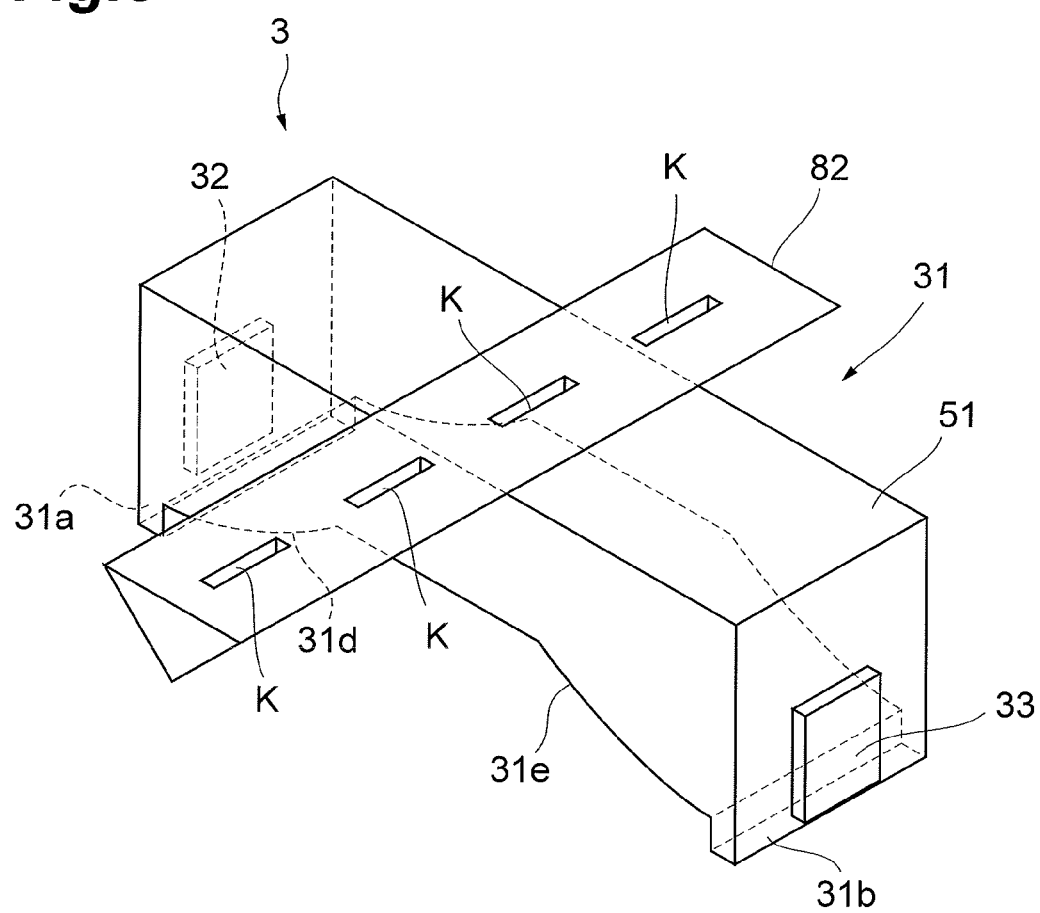
FIG. 8 is a diagram illustrating yet another modified example of the prism part.
Figure 9:
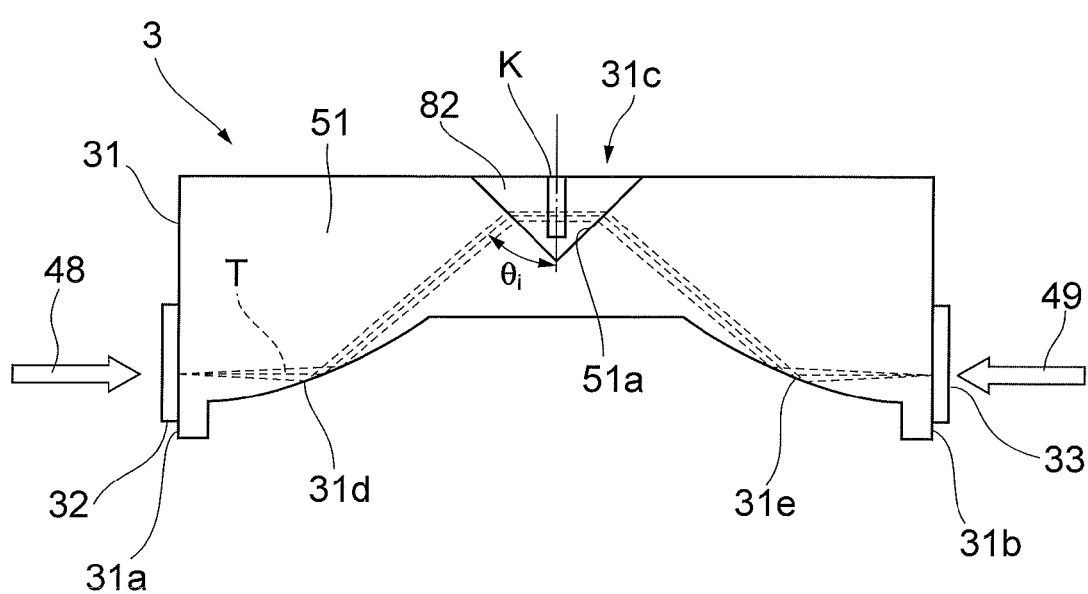
FIG. 9 is a side view of FIG. 8.

Though the above-mentioned embodiment discloses a reflection spectrometer in which the terahertz wave T is reflected by the arrangement surface 31c, a transmission spectrometer in which the terahertz wave T is transmitted through the arrangement surface 31c may be constructed as illustrated in FIGS. 8 and 9, for example. In this case, a prism part 82 is constructed by a material having a refractive index lower than that of the main part 51, while a plurality of (four in this embodiment) grooves are provided at predetermined intervals in the sliding direction in the upper face of the prism part 82 and employed as arrangement regions K to be arranged with the objects 34.

Figure 10:
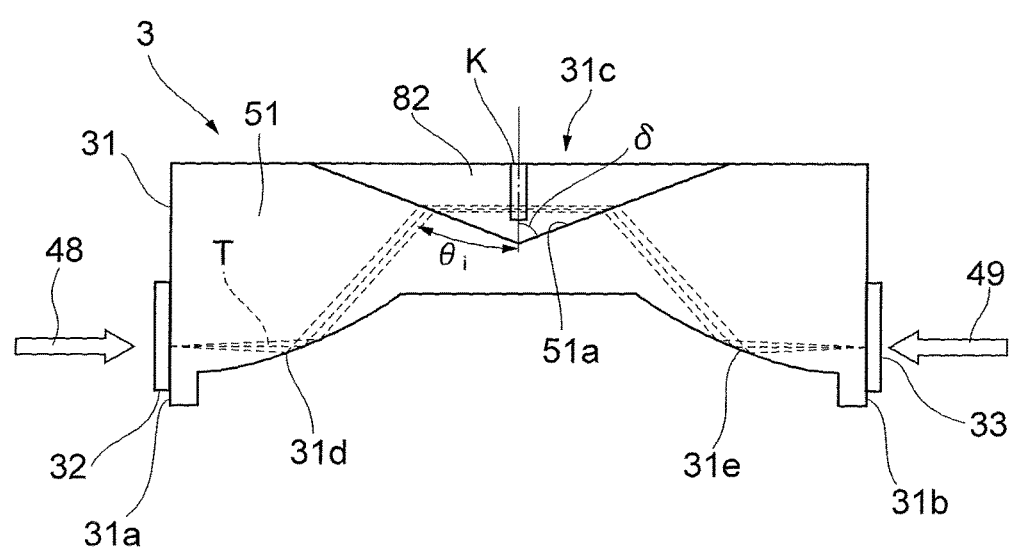
FIG. 10 is a side view of the integral prism in a case where prism parts having forms different from each other mate with each other.

When the incidence angle θi of the terahertz wave T with respect to the spectroscopic prism 31 is 45° in the case where the spectroscopic prism 31 is made of Si having a refractive index of 3.4 while the prism part 82 is made of a plastic having a refractive index of 1.5, for example, the opening angle δ of the groove 51a having the triangular cross section may be 69° as illustrated in FIG. 10. Here, the terahertz wave T is refracted by the mating part between the main part 51 and the prism part 82, so as to be substantially perpendicularly incident on the object 34 within the arrangement region K. The terahertz wave T transmitted through the object 34 is refracted by the mating part between the main part 51 and the prism part 82, so as to return to the same path as in the case of mating with the prism part 52, and is reflected by the second optical surface 31e, so as to exit from the exit surface 31b. Here, a tolerance of about ±1° is permitted.

Such a structure also allows the prism part 82 to slide, after completing the measurement of optical constants for one object 34, so as to shift the next object 34 onto the optical path of the terahertz wave T, whereby a plurality of objects 34 can be measured smoothly.

REFERENCE SIGNS LIST

1 . . . terahertz-wave spectrometer; 2 . . . laser light source; 3 . . . integral prism; 13 . . . beam splitter (branching unit); 31 . . . spectroscopic prism; 31a . . . entrance surface; 31b . . . exit surface; 31c . . . arrangement surface; 32 . . . terahertz-wave generator; 33 . . . terahertz-wave detector; 34 . . . object to be measured; 48 . . . pump light; 49 . . . probe light; 51, 61, 71 . . . main part; 52, 62, 72, 82 . . . prism part; 62c . . . lug; K . . . arrangement region; L . . . reference region; S . . . space; T . . . terahertz wave

The invention claimed is:
1. A terahertz-wave spectrometer comprising:
a light source for emitting laser light;
a branching unit for splitting the laser light emitted from the light source into pump light and probe light;
a terahertz-wave generator for generating a terahertz wave in response to the pump light incident thereon after branching off at the branching unit;
a spectroscopic prism, having entrance and exit surfaces for the terahertz wave and an arrangement surface for one or more objects to be measured, for propagating therewithin the terahertz wave incident on the entrance surface, causing the arrangement surface to reflect or transmit therethrough the terahertz wave, and then emitting the terahertz wave from the exit surface; and
a terahertz-wave detector for receiving the terahertz wave emitted from the exit surface of the spectroscopic prism and the probe light branching off at the branching unit and detecting a correlation between the terahertz wave and the probe light,
wherein, in the spectroscopic prism, a prism part including the arrangement surface is configured to slide with respect to a main part in the width direction of the main part in a direction intersecting the optical path of the terahertz wave transmitted through the spectroscopic prism, while a plurality of arrangement regions to be arranged with the one or more objects are provided in the arrangement surface in the prism part along a sliding direction, the arrangement surface thus being configured so that after completing the measurement of one object the prism part can be slid so as to shift the next object onto the optical path of the terahertz wave so that a plurality of objects can be measured smoothly and continuously,
wherein the main part is provided with a groove into which the prism part including the arrangement surface is slidably fitted, and
wherein the prism part has a surface contacting the main part.

2. A terahertz-wave spectrometer according to claim 1, wherein the arrangement surface in the prism part is further provided with a reference region to be arranged with no object.

3. A terahertz-wave spectrometer according to claim 1, wherein the prism part is provided with a lug.

4. A terahertz-wave spectrometer according to claim 1, wherein a space exists in a part between the prism part and the main part.

* * * * *